(12) United States Patent
Gachet

(10) Patent No.: US 11,449,129 B2
(45) Date of Patent: Sep. 20, 2022

(54) MULTISENSORY CASE AND IMMERSIVE DEVICE

(71) Applicant: THE LAB IN THE BAG, Vulaines-sur-Seine (FR)

(72) Inventor: Jerôme Gachet, Thoury Ferolles (FR)

(73) Assignee: THE LAB IN THE BAG, Vulaines-sur-Seine (FR)

( * ) Notice: Subject to any disclaimer, the term of this patent is extended or adjusted under 35 U.S.C. 154(b) by 314 days.

(21) Appl. No.: 16/479,366

(22) PCT Filed: Jan. 22, 2018

(86) PCT No.: PCT/EP2018/051459
§ 371 (c)(1),
(2) Date: Jul. 19, 2019

(87) PCT Pub. No.: WO2018/134407
PCT Pub. Date: Jul. 26, 2018

(65) Prior Publication Data
US 2019/0354168 A1    Nov. 21, 2019

(30) Foreign Application Priority Data

Jan. 23, 2017   (FR) ...................................... 1770070

(51) Int. Cl.
*G06F 3/01*     (2006.01)
*A61M 21/02*   (2006.01)
(Continued)

(52) U.S. Cl.
CPC ............. *G06F 3/011* (2013.01); *A61M 21/02* (2013.01); *A63G 31/16* (2013.01); *G06F 3/16* (2013.01);
(Continued)

(58) Field of Classification Search
CPC ................. A63J 25/00; A63J 2005/005; A63J 2005/008; A61M 2021/0016;
(Continued)

(56) References Cited

U.S. PATENT DOCUMENTS 4,603,030 A   7/1986  McCarthy
5,760,873 A   6/1998  Wittek
(Continued)

FOREIGN PATENT DOCUMENTS

DE   4314886 A1   11/1994
WO   9737693 A1   10/1997
(Continued)

OTHER PUBLICATIONS

Translation of WO/2015188211A1 (Year: 2015).*
(Continued)

*Primary Examiner* — Christine H Matthews
*Assistant Examiner* — Joshua Daryl D Lannu
(74) *Attorney, Agent, or Firm* — Leason Ellis LLP

(57) ABSTRACT

The invention relates to a multisensory case comprising at least one odor-diffusing device consisting of at least one odor-diffusing support and a ventilator as well as a device for generating an air flow. The odor-diffusing device and the device for generating an air flow are arranged one above the other. The invention also relates to an immersive device comprising a screen and at least two multisensory cases, each case comprising at least one device for generating air flows and a sound-generating device, and to a control device designed to manage the emission of sound and air by independently controlling each of the cases.

15 Claims, 4 Drawing Sheets

(51) Int. Cl.
  *A63G 31/16* (2006.01)
  *G06F 3/16* (2006.01)
  *A61M 21/00* (2006.01)

(52) U.S. Cl.
  CPC .............. *A61M 2021/005* (2013.01); *A61M 2021/0016* (2013.01); *A61M 2021/0027* (2013.01); *A61M 2021/0044* (2013.01); *A61M 2021/0066* (2013.01); *A61M 2021/0077* (2013.01)

(58) Field of Classification Search
  CPC .......... A61M 21/00; A61M 2021/0077; A61M 2021/0027; A61M 21/02; A61M 2021/0044; A61M 2021/005; A61M 2021/0022; A61M 2021/0066; G06F 3/011; G06F 3/16; A63G 31/16
  See application file for complete search history.

(56) References Cited

U.S. PATENT DOCUMENTS

| | | | | |
|---|---|---|---|---|
| 2003/0089370 | A1* | 5/2003 | Daffer | A61H 35/00 128/201.24 |
| 2010/0030013 | A1* | 2/2010 | Brunelle | A61M 21/02 600/27 |
| 2011/0319180 | A1 | 12/2011 | Lee | |

FOREIGN PATENT DOCUMENTS

| | | | | |
|---|---|---|---|---|
| WO | 2015188211 | A1 | 12/2015 | |
| WO | WO-2015188211 | A1 * | 12/2015 | ............. A47C 7/742 |

OTHER PUBLICATIONS

International Search Report and Written Opinion in Corresponding PCT Application No. PCT/EP2018/051459 dated Mar. 27, 2018. 9 pages.
International Preliminary Report on Patentability in Corresponding PCT Application No. PCT/EP2018/051459 dated Jul. 23, 2019. 6 pages.

* cited by examiner

MULTISENSORY CASE AND IMMERSIVE DEVICE

CROSS-REFERENCE TO RELATED PATENT APPLICATIONS

This application is a U.S. National Stage Application under 35 U.S.C. § 371 of International Patent Application No. PCT/EP2018/051459, filed Jan. 22, 2018, which claims the benefit of priority under 35 U.S.C. Section 119 of French Patent Application number 1770070 filed Jan. 23, 2017, both of which are incorporated by reference in their entireties. The International Application was published on Jul. 26, 2018, as International Publication No. WO 2018/134407 A1.

The invention relates to immersive devices, and more particularly devices in which cases are arranged to produce sensory elements.

An immersive device can be intended to test the behavior of a user of a consumer product, or to facilitate the subsequent evaluation of this product by the user. Consumer products are often evaluated by users under conditions that do not reproduce the actual environment in which they are used. This is, for example, the case when the products are submitted to panels in a laboratory. In this case, the user is generally bothered by the fact that the testing conditions do not correspond to the ecological usage conditions. The user can further be disrupted by the interactions with the observers. The user's behavior therefore may not correspond to the behavior he would have in a real environment.

An immersive device can make it possible to improve the behavioral test or the marketing evaluation by allowing the user to test the consumer product in an appropriate environment.

As a non-limiting example, it is possible to propose to test the fragrance of a sun screen in an immersive device where beach images and a corresponding sound are projected, or to test the taste of a food in an immersive device where images of a restaurant and a corresponding sound are projected.

The known immersive devices combine the projection of images and sounds around the user. One or several screens are provided and sound-generating speakers have been distributed at several points of the room in which the device is installed, which makes it possible to create realistic sound effects, i.e., appropriate for what is projected on the screen(s).

These immersive devices can also be implemented for audiovisual recreation and entertainment applications, and in these applications users' demands are increasingly challenging.

Yet in the known devices, user immersion is not complete, since it relates to only two senses, namely sight and sound.

Immersive devices are also known in which an additional sensory effect is generated other than sound, namely wind or odors. One problem of the known devices is that the emission source of the additional sensory effect is periodic, which makes the sensory immersion relatively ineffective.

Yet the most complete immersion is sought irrespective of the desired application for these immersive devices.

In this context, the invention aims to propose an alternative to the existing equipment to produce these immersive devices and in a manner corresponding to an alternative to the known immersive devices.

To that end, the invention proposes a multisensory case and an immersive device.

According to a first aspect of the invention, a multisensory case comprises at least one odor-diffusing device made up of at least one odor-diffusing support and a ventilator. The case further includes a device for generating an air flow, the odor-diffusing device and the device for generating an air flow being arranged one above the other.

According to various features of the invention, considered alone or in combination, it is possible to provide that:
  the device for generating an air flow is arranged above the odor-diffusing device;
  the multisensory case comprises a plurality of sensory devices, including the odor-diffusing device and the device for generating an air flow, arranged vertically one above the other;
  the plurality of sensory devices are arranged such that the device for generating an air flow is directly above the odor-diffusing device;
  the multisensory case comprises a plurality of odor-diffusing devices, each odor-diffusing device comprising a dedicated ventilator;
  the device for generating an air flow is shared by all of the odor-diffusing devices;
  a mister is associated with the device for generating an air flow;
  the multisensory case comprises a device for generating an additional air flow;
  the device for generating an additional air flow is associated with a heat treatment device made to pass through the device for generating an additional air flow; heat treatment device refers both to protecting a heating device and an air conditioning device, or the combination of the two;
  the sensory devices are arranged such that a device for generating low-frequency sounds is arranged below the device for generating an additional air flow, which in turn is arranged below a device for generating high-frequency sounds;
  the multisensory case comprises a light-generating device;
  the light-generating device is configured so as to emit a light beam above the multisensory case;
  the multisensory case comprises a support frame for the sensory devices;
  the sensory devices are configured to emerge and emit on a same face of the frame.

According to a second aspect of the invention, an immersive device comprises a screen and at least two multisensory cases, each case comprising at least one device for generating an air flow and a sound-generating device. Furthermore, a control device is configured to manage the emission of sound and air by independent control of each of the cases.

In particular, the immersive device can comprise a multisensory case as previously described.

In other words, the invention proposes an immersive device comprising a screen, which can be curved, and a plurality of multisensory cases that delimit, with the screen, an immersive zone, the different multisensory cases being arranged on the periphery of the immersive zone, each multisensory case comprising at least one device for generating an air flow and a sound-generating device, as well as a control device that is configured to manage the emission of sound and air through independent control of each of the multisensory cases. Periphery means that the multisensory cases border the immersive zone, both on the side of and above the immersive zone in which the user is led to move.

According to the various features of the immersive device according to the invention, considered alone or in combination, it is possible to provide that:
  the multisensory device comprises a central case arranged between the at least two multisensory cases;

the immersive device comprises a screen support and multisensory cases arranged on either side of the screen, the support comprising a bar arranged between the two cases to support the central case;

the central case comprises a ventilator configured to redistribute the air mixed by the devices for generating an air flow arranged in each multisensory case;

the screen is curved; curved screen is meant to cover both the fact that the curvature of the screen is regular and the fact that the curvature of the screen is complex, with facets; by extension, it is possible to provide that the screen is made up of a plurality of flat screen portions inclined angularly relative to one another so as to reproduce a globally curved assembly;

the at least two multisensory cases comprise two side multisensory cases respectively in the extension of the ends of the curved screen;

the immersive device comprises a plurality of multisensory cases that delimit an immersive zone with the screen;

the central case is arranged at the center of and above the immersive zone; "at the center" of the immersive zone means that the width of the immersive zone is defined by the separation between two side cases arranged near the screen, and that the central case is arranged on the median line between these two side cases; "above" means that the central case overhangs the user placed in the immersive zone;

the screen is associated with an image projection device; and the image projection device is an overhead projector arranged on the side of the screen opposite the immersive zone;

the immersive zone comprises two so-called front multisensory cases, arranged in the direct vicinity of the screen, two so-called rear multisensory cases, arranged at the opposite end of the immersive zone, and a central case;

the control module is configured for a balanced distribution of the effects between each of the multisensory cases as a function of the image on the screen.

Other features and advantages of the present invention will appear more clearly using the description and drawings, among which:

Figure 1:
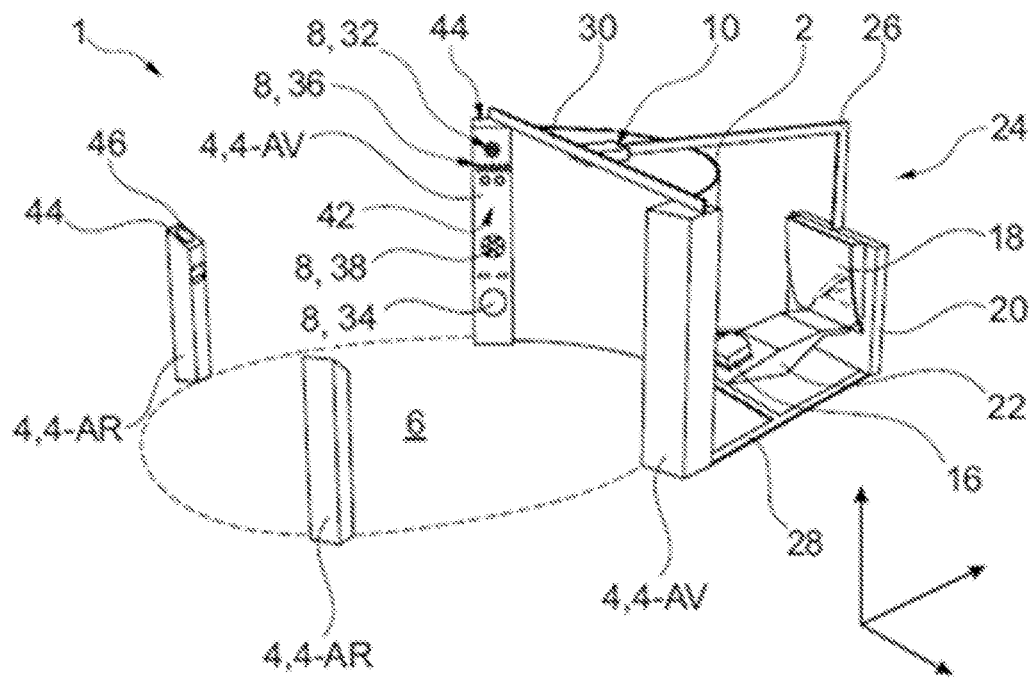
FIG. 1 is a perspective overview of an immersive device equipped with a plurality of multisensory cases and a screen delimiting an immersive zone, the perspective also showing an overhead projector device configured to emit images on the screen.

It should be first be noted that the figures lay out the invention in detail in order to carry out the invention, said figures of course being able to be used to better define the invention if needed. However, it should be noted that these figures only lay out a portion of the possible embodiment variants according to the invention.

In the description that follows, reference will be made to an orientation using longitudinal L, vertical V and transverse T axes, as they are defined arbitrarily using the trihedron L, V, T shown in the figures. In particular, the vertical axis V corresponds to the direction perpendicular to the ground, such that the positions below or below will be defined as a function of the verticality along this vertical axis V.

An immersive device 1 according to one aspect of the invention includes at least one screen 2, serving as projection medium for an image or a video, and at least two multisensory cases 4 configured to emit several sensory effects as a function of the image simultaneously projected on the screen. The purpose of such a device is to offer an immersive experience to a user, whether in a recreational, professional or medical context. In order to best take advantage of the sensory experience, the user is in a seated position or a standing position in an immersive zone 6 defined by the position of the multisensory cases 4, advantageously in front of or behind him and on each of his sides, and by the position of the screen 2. The plurality of multisensory boxes delimits, with the screen, the size and shape of this immersive zone, and therefore indirectly the number of users able to use this immersive zone at one time.

In the illustrated example, the immersive device 1 comprises at least four multisensory cases 4 according to one aspect of the invention, namely cases of the column type in which sensory devices 8 on board this case are stacked vertically one above the other. Hereinafter, we will describe specific arrangements of the sensory devices in these column-type cases.

Among the four multisensory cases, a distinction is made between two first multisensory cases, called front multisensory cases 4-AV, arranged in the immediate vicinity of the screen 2, two second multisensory cases, called rear multisensory cases 4-AR and which are arranged at the opposite end of the immersive zone 6 relative to the screen 2 and the first multisensory cases, and a central case 10, arranged in the vicinity of the screen 2 and between the two front multisensory cases 4-AV.

The immersive device further comprises at least one control device in order to control the multisensory cases 4, which advantageously to that end includes a main control module 12, and a plurality of specific control modules 14, dedicated to each of the multisensory cases 4.

The main control module 12 is configured to define, for a defined moment of the video projected on the screen, a plurality of control instructions respectively dedicated to one and/or the other of the sensory devices, and to one and/or the other of the multisensory cases. The control modules, whether main or specific, are configured to manage the emission of sensory elements by an independent control of each of the cases, so as to provide a balanced distribution of the sensory effects between each of the multisensory cases as a function of the image on the screen.

A balanced distribution of the effects between each of the cases means that it is possible, as a function of a first image on the screen, for each of the cases to be controlled so as to perform the same sensory emission in the same proportions, and as a function of a second image, for only one of the cases to be controlled in order to perform a sensory emission while the others remain inactive.

As will be described hereinafter, a multisensory case 4 according to the invention can comprise a plurality of sensory devices 8 stacked one above the other, so as to provide varied sensory effects so that the user has at least one auditory, olfactory or haptic sensation in addition to the visual sensation provided by the projection of images on the screen.

The screen 2 can in particular consist of an image projection medium, associated with an image projection device 16, for example of the video projector or overhead projector type.

As illustrated, the screen is associated with an image projection device of the overhead projector type. In this way, the image projection device 16 is arranged behind the screen and it is not present in the immersive zone. This results in a better immersion for the user, who on the one hand does not see the device forming the source of the images projected on the screen and on the other hand does not hear, or only slightly hears, the continuous blowing due to the operation of the projector.

As illustrated, the overhead projector can be associated with a mirror 18 in order to improve the compactness of the immersive device 1. The overhead projector emits a beam of light opposite the screen, and this beam is reflected by the mirror toward the rear face of the screen 2, i.e., the face opposite the immersive zone 6. The overhead projector is then arranged between the screen 2 and the mirror 18 and it is not necessary to have too much distance for the projected image to spread out over the entire screen.

In an embodiment variant illustrated in FIG. 8 and which will be described below, the image projection device can consist of a video projector arranged above the screen, at least partially above the immersive zone. This arrangement makes it possible to project the image on the screen without the presence of a user at the center of the immersive zone bothering the projection of images, and makes it possible to limit the bulk, or to free zones for the control electronics in particular, behind the screen.

In this context, the position of the mirror 18 is defined relative to the screen 2, then the position of the projector 16 is defined relative to the mirror 18. The mirror is fastened on a first platen 20 and the projector is fastened on a second platen 22, both platens being able to be part of a same part, such that the relative position of the projector with respect to the mirror is already known and all that remains is to adjust the position of the mirror with respect to the screen. A support 24, visible in FIGS. 1 and 2, can facilitate the fastening of the mirror with respect to the screen, to guarantee a reliable position and therefore a sharp image upon each installation of the immersive device, without it being necessary to adjust the distortion of the image upon each installation.

The support in particular comprises a support beam 26 connecting the center of the screen 2, and if applicable the upper part of a chassis supporting the screen, the first platen 20 supporting the mirror. In this way, the transversely centered position of the mirror, and therefore the projector, is defined with respect to the screen, and the implementation of the separation between the mirror and the screen is ensured as it was theoretically defined as a function of the adjustment of the distortion established beforehand.

The support can further comprise a base 28, called upon to be placed on the ground and which makes it possible to connect the first platen 20 supporting the mirror on the one hand to the front multisensory cases 4-AV and on the other hand to a lower part of the chassis supporting the screen. One thus simultaneously ensures the proper relative position of the screen and the mirror belonging to the projection system, for the sharpness of the images, as well as the proper position of the multisensory cases relative to the projected images.

As has just been specified, the screen can be supported by a chassis, which assumes a curved shape making it possible to mold the screen. It can in fact be interesting, in order to enhance the immersive effect for the user, to condition it in an immersive zone delimited by a curved screen. The chassis includes an upper part and a lower part on which the upper and lower edges of the screen 2 are stretched.

These upper and lower parts of the chassis can be fastened at each of their side ends to a vertical gantry defining the side edge of the screen, and it will be understood that in the illustrated example, without this being limiting with respect to the invention, the upper and lower parts of the screen chassis are respectively fastened, in particular by a quarter-turn screwing system, on the front multisensory cases 4-AV arranged on either side of the screen 2.

Figures 2, 3:
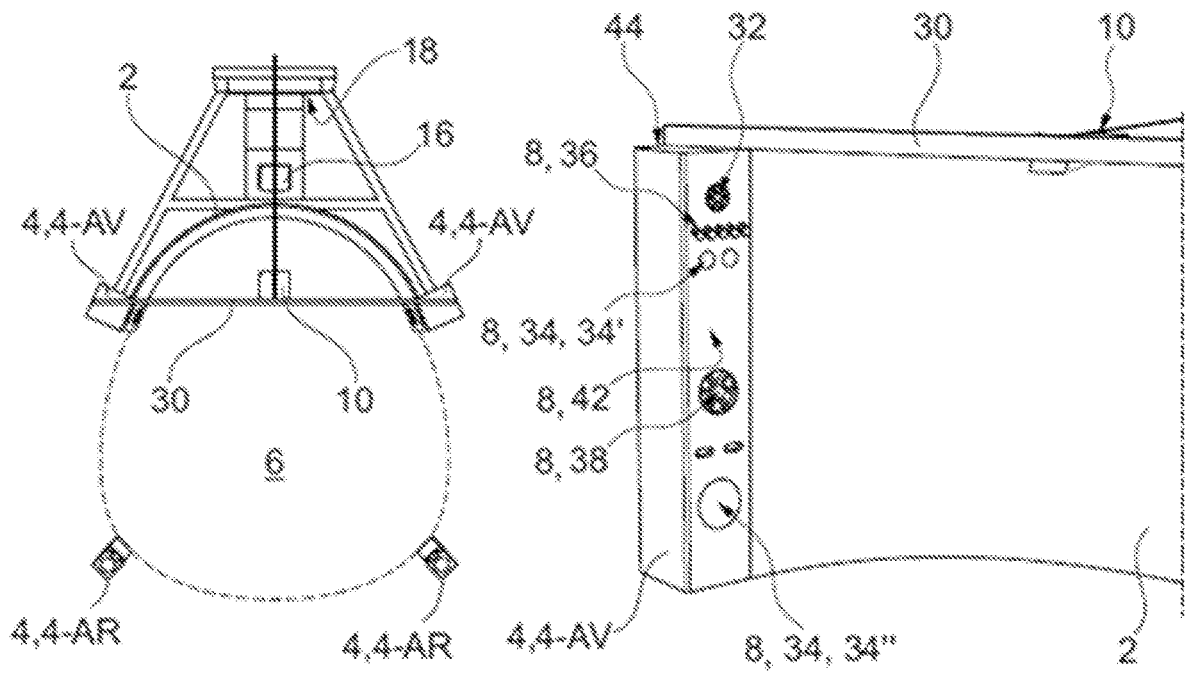
FIG. 2 is a top view of the immersive device of FIG. 1.
FIG. 3 is a detailed view of a multisensory case equipping the immersive device of FIG. 1.

As illustrated in FIG. 2, the two front multisensory cases 4-AV arranged on either side of the screen are respectively arranged in the extension of the ends of the screen 2, which here is curved.

The screen is curved in particular so that the entire surface of the screen is at an equivalent distance from the user placed at the center of the immersive zone, which minimizes the eye strain of the user and maximizes his viewing comfort and therefore his immersion.

The support can comprise a bar 30 arranged between the two front multisensory cases 4-AV, and which rests at its transverse end on the apex of the cases, so as to extend above the screen. This bar of the support is configured to carry, substantially in its center, a support frame in which the central case 10 is arranged. In this way, the central case 10 is positioned at the center of and above the immersive zone 6.

In the previously mentioned embodiment variant, the video projector, forming the projection device 16 able to project an image on the side of the screen corresponding to the immersive zone, can be mounted on this bar 30. It should also be noted that the fact that the bar 30 rests on the transverse ends on the apex of the cases could be modified without going beyond the context of the invention, in particular by placing a gantry that will be described hereinafter in more detail.

The various multisensory cases 4 are positioned on the periphery of the immersive zone, and it should be noted that each case comprises at least one device for generating an air flow 32 and a sound-generating device 34, in the context of sensory devices 8 stacked on one another in a column-type case.

Figure 5:
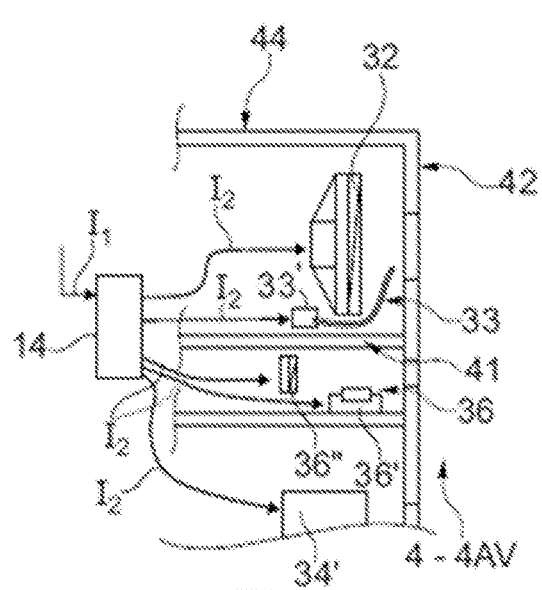
FIG. 5 is a partial cross-sectional view along plane A-A of FIG. 4 of a multisensory case of a first type.

In the exemplary embodiment presently described and in particular illustrated in FIG. 5, it should be noted that each of the multisensory cases 4 comprises, in the context of sensory devices stacked on one another in a column-type case, at least one device for generating an air flow 32, a sound-generating device 34, as well as an odor-diffusing device 36, and that the central case 10 comprises at least one of these same sensory devices.

The central case 10 in particular comprises a central ventilator 10' configured to redistribute the air mixed by the devices for generating an air flow 32 arranged in the front multisensory cases 4-AV, positioned on either side of the screen 2. For example, the devices for generating an air flow 32 arranged in each front multisensory case are respectively oriented toward the central case.

As will be described in more detail hereinafter, it is in fact possible to note that each of the sensory devices can be arranged within a multisensory case 4 so as to emit in a given direction, which can be different from the direction in which another sensory device of the same case emits, or different from the direction in which an equivalent sensory device of another case emits. As an example, the sound-generating devices of each of the multisensory cases will be arranged so that the sound is emitted toward the center of the immersive zone, while the air flow and the odors emitted by the front multisensory devices will be oriented toward the central case in order to be mixed via the ventilator of this central case.

A canvas can be stretched in the extension of the screen to hide the junction between the screen and the front multisensory cases, i.e., the cases that are most likely to be perceived by the user looking at the screen. This canvas can trim the case, at least on the zones on which there are no outlets of the sensory device, in a color close to what is projected on the screen.

It is further possible to provide additional protection means making it possible to produce video mapping, by means of which an image background is projected that is complementary to the images projected on the screen.

We will now provide a more detailed description of the multisensory case 4 forming part of an immersive device according to the invention, in reference in particular to FIGS. 3 to 6.

A multisensory case 4 comprises a frame 40 forming a support for sensory devices. The frame is generally in the shape of a column, in the illustrated case with a square cross-section, and this frame comprises a plurality of supports 41 for positioning the sensory devices 8. As an example, and as is illustrated in FIG. 5, the case is in the form of a shelf with several trays forming a support 41 that are superimposed and on which the sensory devices 8 and the associated specific control modules 14 are positioned.

It is possible to define a front face 42 of the frame as the face intended to be turned toward the center of the immersive zone, when the set of cases is placed around or near the screen. The sensory devices are configured to emerge and to emit primarily on a same face of the frame, namely this front face of the frame. However, one could understand that without going outside the scope of the invention, one or several sensory devices could have an outlet arranged in a face directly adjacent to this front face.

Each case according to aspect of the invention comprises a plurality of sensory devices 8, generating distinctive sensory effects, positioned vertically one above the other, so as to form a column-type case.

Preferably, the dimensions of the frame 40 in order to form a column-type case intended to be installed in front of or behind the immersive zone 6 are substantially the same regarding the definition of the base of the case, and for example around 50 cm for its width and for its depth, and vary to define the height of the case. The height can thus be equal to 2.10 m for the front multisensory cases 4-AV, and equal to 1.4 m for the rear multisensory cases 4-AR.

As will be described hereinafter, the front 4-AV and rear 4-AR multisensory cases can differ, aside from their height, by the shape of their front wall 44, with a wall parallel to the ground for the front multisensory cases and an inclined wall relative to the ground for the rear multisensory cases.

Figure 4:
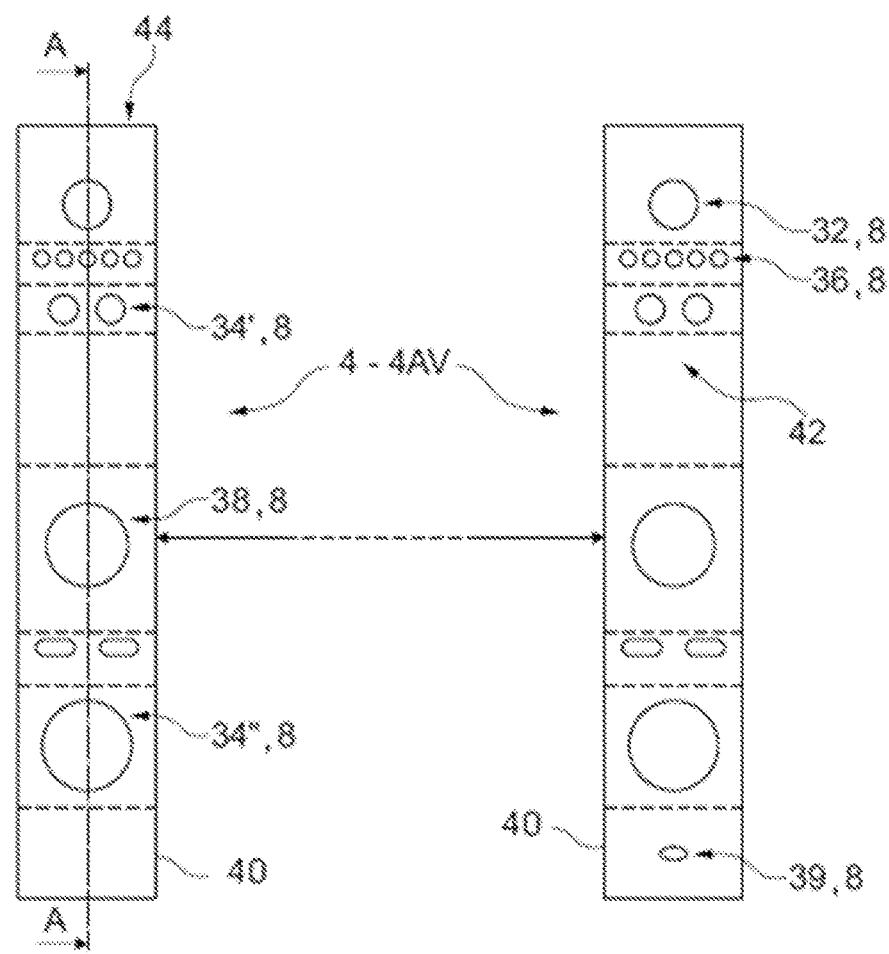
FIG. 4 is a schematic front view of two multisensory cases of a first type as illustrated in FIG. 3.

First, reference will in particular be made to FIGS. 3 to 5 in order to describe a front multisensory case 4-AV.

As illustrated example, a multisensory case can include, from top to bottom, a device for generating an air flow 32, an odor-diffusing device 36, a device for generating high-frequency sounds 34', a device for generating an additional air flow 38 and a device for generating low-frequency sounds 34".

The odor-diffusing device 36 is formed by at least one odor-diffusing support 36' and a ventilator 36", as visible in FIG. 5. In the illustrated example, it is provided to equip the front multisensory cases 4-AV (FIG. 4) with five odor-diffusing devices 36, and to equip the rear multisensory cases 4-AR (FIG. 6) with two odor-diffusing devices 36.

For each of the odor-diffusing devices 36, the odor-diffusing support 36' consists of a reservoir containing a perfumed substance, the reservoir being able to be opened or closed using a solenoid valve. It is understood that when the reservoir is open, the fragrance exuded therefrom is set in motion by the ventilator.

In the multisensory case, one can see the ventilator 36", specifically dedicated to an odor-diffusing device 36 and a diffusion support 36', and the device for generating an air flow 32, which is arranged separately from the odor-diffusing device(s) 36. The ventilator 36" associated with the diffusion support is triggered only when the reservoir is open and releases a scented substance. The ventilator is thus arranged at the end of a pipe 37 in which the scented substance is released, and the ventilator 36" and the reservoir of the diffusion support 36' are positioned substantially in a same horizontal plane, and according to the invention at a same stage 41 of the column-type multisensory case. The device for generating an air flow 32 is in turn arranged in a vertical horizontal plane different from that in which the diffusion supports 36' and the associated ventilators 36" are arranged, and it can be triggered indifferently from the triggering of the odor diffusion devices 36.

As this has previously been described, the multisensory case 4 here is equipped with a plurality of odor-diffusing devices 36, each odor-diffusing device comprising a specific ventilator 36", and the device for generating an air flow 32 is shared by all of the odor-diffusing devices. Advantageously, the scented substances respectively contained in each of the odor-diffusing devices are different from one another, and the diffusion of a first or an $n^{th}$ odor is controlled as a function of the projected image and the odor that one wishes to associate therewith, by opening a first or an $n^{th}$ reservoir and simultaneously activating a first or an $n^{th}$ ventilator, as well as by activating the odor-diffusing device positioned above the odor-diffusing devices.

It is in fact noteworthy that, in each of the multi-sensory cases 4 illustrated in the figures, the odor-diffusing device 36 and the device for generating an air flow 32 are positioned one above the other. In particular, the device for generating an air flow is positioned above the odor-diffusing device. More specifically, while a multisensory case 4 according to one aspect of the invention comprises a plurality of sensory devices including at least one separate from the device for generating an air flow and the odor-diffusing device as they have just been described, these sensory devices 8 are arranged such that the device for generating an air flow 32 is directly above the odor-diffusing device 36.

This arrangement makes it possible to push the scented substance, set in motion by the ventilator and rising at the outlet of the front face 42 of the case, toward the center of the immersive zone 6, through the effect of the device for generating an air flow. It also makes it possible to position, in this context, the device for generating an air flow 32 of each multisensory case above the heads of the users, such that the air flow and the scented substance that it brings with it pass above the users, making the olfactory sensation more diffuse and less aggressive.

It will be understood that, moreover, the device for generating an air flow 32 can be activated without the odor-diffusing device 36 being activated, only to produce a sensory effect illustrating the presence of air, wind, without specific odors.

The front and rear multisensory cases can next differ in terms of the number and arrangement of the sensory devices that they comprise.

The front multisensory case 4-AV comprises a device for generating an additional air flow 38, in particular used to produce a complementary air flow when the images on the screen require it, in order to optimize the immersion of the user, a significant air flow that the device for generating an air flow arranged above the odor-diffusing device cannot implement alone. This device for generating an additional air flow 38 is arranged in the lower part of the column-type case, and can if necessary be used when the immersion requires creating a puff along the ground.

The device for generating an additional air flow 38 is dedicated solely to generating an air flow to reproduce the effect of the wind, whereas, as was previously specified, the device for generating an air flow 32 positioned in the immediate vicinity of the odor-diffusing device 36 is bifunctional in that it makes it possible to diffuse the generated odors and in that it makes it possible to participate in reproducing the effect of the wind. The device for generating an air flow 32 is primarily implemented, and the device for generating an additional air flow 38 is only implemented when the need for air exceeds what the device for generating an air flow can deliver.

The presence of a device for generating an air flow 32 and a device for generating an additional air flow 38 makes it possible, aside from the offered possibility of quantifying the force of the generated air flow on the whole, to qualify the air flows differently depending on the immersive needs.

As an example, one or several high-pressure misters 33 are associated with the device for generating an air flow 32, and a heat treatment device is associated with the device for generating an additional air flow 38 so as to heat or cool the air made to pass through this device for generating an additional air flow. It is then possible on the one hand to produce a haptic effect by projecting droplets on the user's skin, by turning on the device for generating an air flow and the mister(s), the mouths of which are positioned as close as possible to the blades of this device for generating an air flow, and on the other hand to produce another haptic effect by a sensation of heat or cold by activating the device for generating an additional air flow and its associated heat treatment device. It will be understood that, in each of these cases, the control module 14 specific to the multisensory case is configured to send an activation instruction for each of the components separately, so as to be able to trigger the device for generating an air flow 32 with or without simultaneously starting up the mister, and to be able to trigger the device for generating an additional air flow 36 with or without simultaneously starting up the heat treatment device of the air.

The mister(s) 33 can consist of high-pressure spray nozzles, for example at 15 bars, for a liquid coming from a liquid storage source 33', arranged near the nozzles. These nozzles are positioned as close as possible to the front face 42 of the frame such that the liquid leaving the nozzles is sprayed immediately in the form of droplets under the effect of the air flow blown by the device for generating an air flow 32.

The heat treatment device associated with the device for generating an additional air flow 38 can consist of an electric heating system, optionally with a resistance molded from ceramic, and/or an air conditioner.

The front multisensory cases 4-AV also comprise a sound-generating device 34 that is specific in that it includes a plurality of speakers positioned at a distance from one another, and in particular a device generating high-frequency sounds 34' and a device generating low-frequency sounds 34".

Following on the preceding, the sensory devices 8 are arranged such that the device generating low-frequency sounds 34" is positioned below the device generating an additional air flow 38, which is positioned below the device generating high-frequency sounds 34'. Additionally, the device generating high-frequency sounds is positioned approximately at person height, with the understanding that to that end, one can use the average height of men and women in the country of use of the immersive device, which for France is, for example, substantially equal to 1.68 m.

The parts of the case containing the sound generating devices, whether high or low frequency, can is covered by a fabric, so as to make these devices invisible by the user, without this bothering the propagation of the sound.

Furthermore, in this context of camouflage of the multisensory cases, it is possible to provide that the ventilation mouths of the devices for generating an air flow 32 and additional air flow 38 can be closed by removable systems, so that these devices are not visible when the system is not in use.

On at least one of the multisensory cases, and in particular, in the case illustrated in FIG. 4, on one of the front multisensory cases, it is also possible to provide a smoke generator 39, the activation of which is also controlled by a control module specific to the case.

Figure 6:
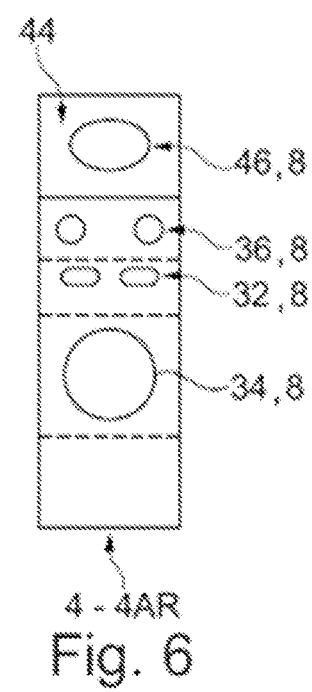
FIG. 6 is a schematic front view of a multisensory case of a second type.

Secondly, reference can be made to FIG. 6 to describe a rear multisensory case. As has been previously specified and is comprehensible by the schematic comparison of FIGS. 4 and 6, the rear multisensory case differs in particular by its size and the number of sensory devices that it comprises in its frame.

The frame has a different shape in that the upper wall 44, as is visible in FIG. 3, is not parallel to the plane of the ground but inclined, such that the front face intended to be turned toward the immersive zone and by which the sensory devices emerge is not as high as the opposite rear face.

The rear multisensory case further differs in that it comprises a light-generating device 46, configured so as to emit a beam of light above the multisensory case, and therefore above the user. It is thus possible to project, on a ceiling of the room in which the immersive device is positioned, or on a canvas stretched above the immersive zone, an ambient light able to evolve as a function of the image projected on the screen.

The light-generating device 46 consists of a multicolored lighting device, which can in particular be made up of a multitude of light-emitting diodes. Thus, the dominant color of the different scenes of the video projected on the screen is projected in light form.

It is also possible to note the difference made by the fact that only one low-frequency sound generating device 34" is provided in the multisensory cases.

Conversely, and according to what was described for the front multisensory cases, the rear multisensory cases 4-AR comprise a device for generating an air flow 32 and an odor-diffusing device 36 that are stacked one directly above the other, i.e., without sensory devices interposed between them, in a column-type case, with the set of stacked sensory devices. Contrary to what is proposed in the front multisensory cases, and because of the height at which the odor-diffusing device(s) can be arranged in a rear multisensory case, the device for generating an air flow here is positioned below the odor-diffusing device(s) in order to facilitate the perception of odors by the user.

In this way, the immersive device according to the invention comprises cases for multipoint emission, i.e., emitting simultaneously from several locations around the user present in the immersive zone, different sensory effects in a manner synchronized with the diffusion of images on a screen participating in delimiting this immersive zone.

According to the present example, shown in particular in FIG. 2, it is possible to provide a first group of two front multisensory cases 4-AV, having a same first height, and a second group of two rear multisensory cases 4-AR, having a same second height. It is important that for a same group of multisensory cases, the sensory devices are at a same height for a homogeneity of the sound and the other sensory elements. In other words, it matters that the odor-diffusing devices positioned in a multisensory case to the left of the screen are located at the same height relative to the ground as the odor-diffusing devices positioned in a multisensory case to the right of the screen.

The rear multisensory cases can be smaller, and comprise fewer sensory devices than in the front multisensory cases, but according to the invention, it matters that each case has a column shape with the sensory devices that it comprises stacked one above the other.

Figure 7:
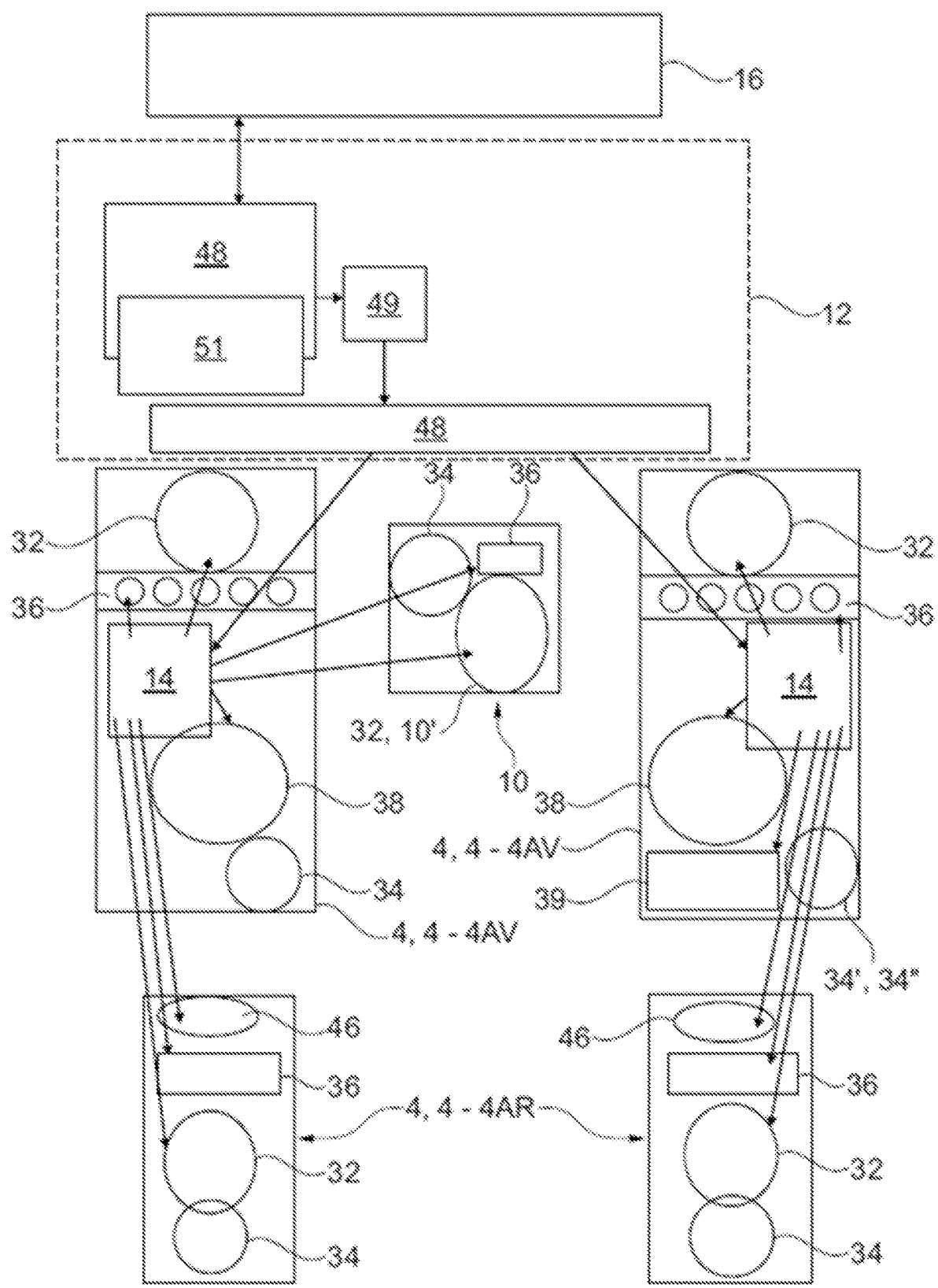
FIG. 7 is a schematic illustration of an immersive device illustrating the control of the sensory devices equipping the multisensory cases via a plurality of associated control modules.

We will now provide a more detailed description of the control of the various sensory devices so that they emit sensory effects in a synchronized manner with the image projected on the screen and in several different locations around the user, so as to produce a successful immersive effect, in reference in particular to FIG. 7.

The immersive device 1 comprises a main control module 12 connected to the projection device 16 on the one hand, and to the set of sensory devices 8 on the other hand. The main control module 12 comprises a computer 48 that is on the one hand connected to the projection device 16 and that is moreover connected to a digital multiplexing interface 50 preferably of the DMX type, for example via a wired connection 49 of the USB type.

The computer 48 of the main control module 12 is implemented with a track 51 modeling the sequence of images or the video projected on the screen and associating, at each moment of the total duration of this track, sensory effects to be produced in concordance with the projected image. The control module is thus able to control all of the sensory devices present in each of the multisensory cases as a function of the image projected on the screen.

The digital multiplexing interface 50, or DMX distributor, simultaneously sends to DMX receivers 52, or contactors, respectively on board in each of the multisensory cases 4, general control instructions 11 for each of the cases present in the corresponding case.

The receiver or contactor 52 is implemented in a control module 14 specific to each case that subsequently dispatches specific control instructions for each of the sensory devices, and in particular start/stop instructions for these devices.

In the illustrated example, general control instructions 11 are sent simultaneously to the left and right front multisensory cases 4-AV to the specific control module 14 dedicated to each of the cases. Secondly, the specific control modules 14 send specific first control instructions 12 to each of the sensory devices 8 present in the corresponding front multisensory case 4-AV and specific second control instructions 13 to each of the sensory devices 8 present in the closest rear multisensory case 4-AR.

Furthermore, one and/or the other of the specific control modules sends third specific control instructions 14 to each of the sensory devices present in the central case 10.

In this way, a specific sensory effect emitted in a specific zone can be made to correspond to a given image.

Figure 8:
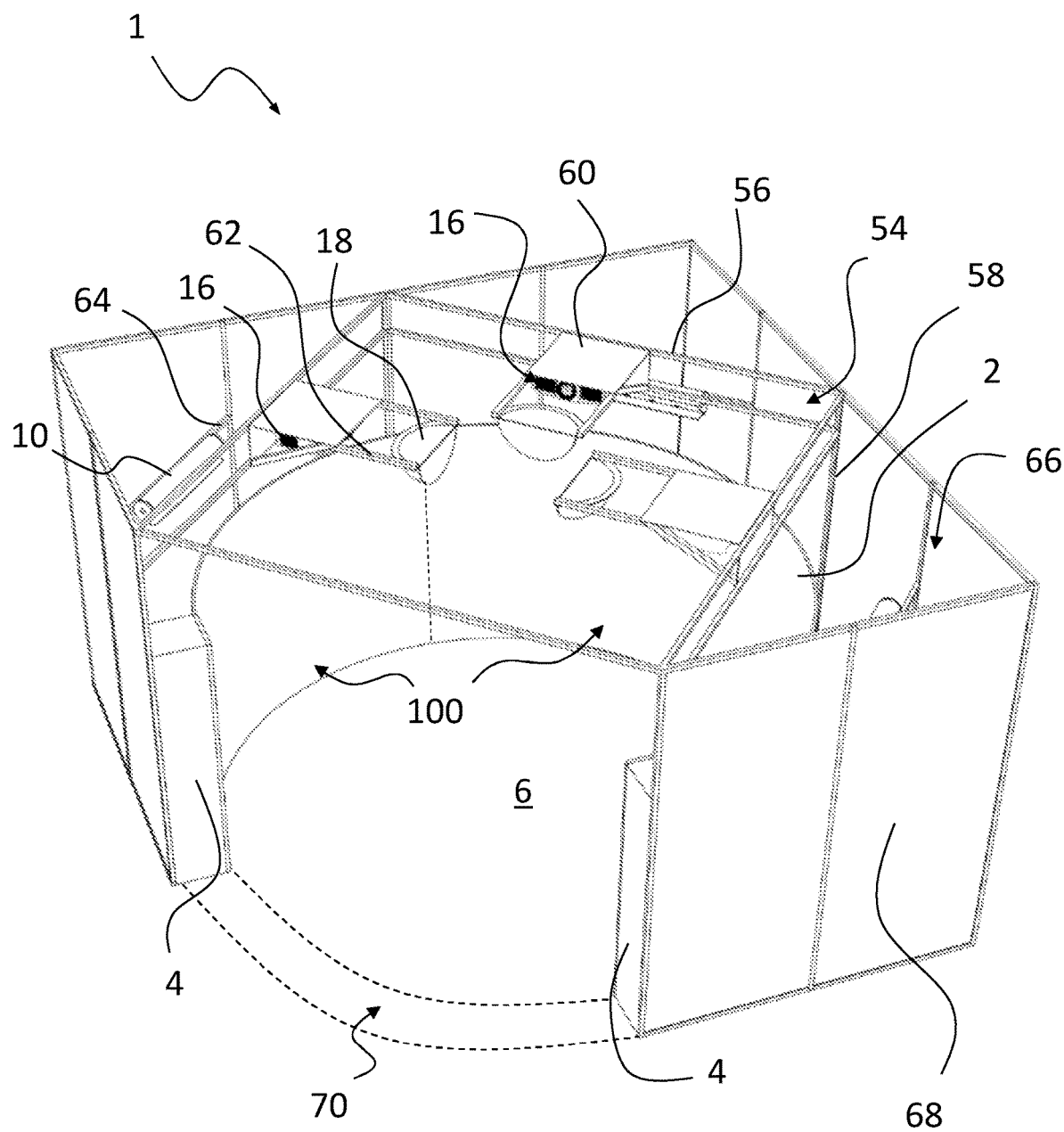
FIG. 8 is a schematic illustration of an embodiment variant of the immersive device according to the invention.

An embodiment variant of the immersive device according to the invention is illustrated in FIG. 8. According to what was described previously, the immersive device 1 comprises a curved screen 2 and a plurality of multisensory cases 4 that define an immersive zone 6. The immersive zone is in particular delimited by the curved screen, and the multisensory cases are positioned on the periphery of the immersion zone. The main multisensory cases, or front cases as previously mentioned, are positioned at the ends on either side of the curved screen, which can in particular consist of a canvas slipped around a curved tubular structure, here not visible because it is covered by the canvas.

The immersive device differs from the preceding in that the curved screen has an arc of circle profile of about 270° and in that here there are two multisensory cases in a column, respectively arranged at each end of the curved screen.

A projection device 16 is specifically associated with a portion of the screen, here extending over 90°, such that three protection devices are provided here, each projection device being configured to project a portion of the overall image on its associated screen portion as it must ultimately be perceived by the user.

Each projection device 16 is mounted on a gantry 54, a central bar 56 of which extends above the portion of the associated screen. More specifically, the gantry has uprights 58, of which there are four here, fastened to the ground and regularly distributed, as well as central bars that connect the uprights two by two, such that each central bar 56 extends above one of the screen portions.

It is understood that one thus forms a plurality of modules 100 having a screen portion with an arc of circle profile of 90°, furthermore with this curved screen portion, uprights between which the central bar extends, and a projection device specific to each module.

In this way, it is possible to provide, without going outside the scope of the invention, an immersive zone of appropriate size for the user's needs, while producing an immersive device 1 by means of one or several modules placed side by side, with a control module of the immersive system that is configured to control the projection devices and to adapt the projection by each projection device for portions of the final image seen by the user as a function of the number of modules placed in series.

In an immersive device according to this embodiment variant, and in particular in the illustrated scenario of a screen curved at 270°, in which a projection system comprises several projection devices, the control module is configured to coordinate these projection devices in order to project a continuous image along the curved screen, if applicable in the image overlap zones projected from one module to the other.

Each projection device here comprises a video projector that is positioned above the immersive zone, the video projector 16 being associated like before with a mirror 18 in order to optimize the bulk. The video projector is fastened on a casing 60 secured to the central bar of the gantry and the mirror is supported at the arm end 62 extending from the casing toward the center of the immersive zone. The projection of images by the video projector is done in a direction opposite the screen and the mirror is arranged to return the image toward the screen, from a position overhanging the immersive zone and near the screen portion that is associated therewith, such that the presence of a user substantially at the center of the immersive zone does not hinder the production of images and does not harm the immersive nature of this projection.

The immersive device comprises a central case 10 specific to each module and which is, in the illustrated example, supported by a bar 64 arranged withdrawn from the screen, above a clearance zone 66. It should be noted that this central case could be positioned overhanging the screen on the central bar, near the support case of the projector.

The clearance zone 66 makes it possible to house electronic equipment, and in particular the control module with, if applicable, a partition 68, here square, to hide these clearance zones. The partition 68 has an opening 70 for access by the user to the immersive zone 6.

We will now describe an exemplary application of the immersive device according to the invention, during which one aims to have a user test a product in an appropriate environment, and for example a tanning oil in an environment representative of a beach.

As is the case for most of the exemplary applications that could be cited, the multisensory cases are controlled so as to nearly systematically generate a diffusion of air and a diffusion of sounds, and therefore simultaneously with the production of any other sensory effect. The sound is diffused continuously, in particular to cover the operating noises of each sensory effect. Additionally, an air flow is diffused both when one wishes to have the user feel the existence of wind and when an olfactory effect is produced, to participate in odor diffusion. The presence of ventilators forming a device for generating an air flow in each of the cases allows an optimal recreation of the perception of wind arriving from any location of the immersive zone and makes it possible to improve an appropriate carrying of the misting and odor effects.

When a projected image corresponds to a palm tree whose leaves move under the effect of the wind, the control module sends an instruction via the DMX interface to each of the devices for generating an air flow, and if applicable to the devices for generating an additional air flow, to generate an air flow representative of a gust of wind causing the leaves to move.

When later, a projected image corresponds to a wave formed under the effect of a stronger wind, the control module sends, via the DMX interface, instructions to each of the devices for generating an air flow, and, if applicable, to the devices for generating an additional air flow, to generate an air flow representative of this stronger gust of wind and other instructions to each of the misters to generate the formation of droplets dispersed by the device for generating an air flow so that the user feels the moisture formed by the wave.

The user can thus truly feel like he or she is at the beach, in the situation where the product to be tested would be used, so as to be completely invested in testing the product.

Other applications could be implemented, for example recreational or medical applications.

The invention claimed is:

1. A multisensory case comprising at least one odor-diffusing device made up of at least one odor-diffusing support and a dedicated ventilator, wherein the multisensory case columnar in form and includes a plurality of sensory devices that are stacked vertically one above the other, one of the sensory devices being formed by the at least one odor-diffusing device and wherein the multisensory case further includes a device for generating an air flow, the at least one odor-diffusing device and the device for generating an air flow being arranged separately one above the other.

2. The multisensory case according to claim 1, wherein the device for generating an air flow is arranged above the at least one odor-diffusing device.

3. The multisensory case according to claim 1, wherein the plurality of sensory devices includes the at least one odor-diffusing device and the device for generating an air flow, wherein the at least one odor-diffusing device and the device for generating the air flow are arranged vertically one above the other.

4. The multisensory case according to claim 3, wherein the plurality of sensory devices are arranged such that the device for generating an air flow is directly above the at least one odor-diffusing device.

5. The multisensory case according to claim 3, further comprising a support frame for the sensory devices.

6. The multisensory case according to claim 5, wherein the plurality of sensory devices are configured to emerge and emit on a same face of the frame.

7. The multisensory case according to claim 1, wherein each of the at least one odor-diffusing device comprises a dedicated ventilator.

8. The multisensory case according to claim 7, wherein the device for generating an air flow is common to all of the at least one odor-diffusing device.

9. The multisensory case according to claim 8, wherein a mister is arranged next to the device for generating an air flow.

10. The multisensory case according to claim 1, wherein the multisensory case comprises a device for generating an additional air flow that is positioned at a different vertical level in the multisensory case from the device for generating an air flow.

11. The multisensory case according to claim 1, further comprising a light-generating device.

12. An immersive device comprising the multisensory case according to claim 1.

13. The immersive device according to claim 12, further comprising a screen and at least two multisensory cases, each case comprising the device for generating an air flow and a sound-generating device, as well as a control device that is configured to manage an emission of sound and air by independent control of each of the multisensory cases.

14. A multisensory case comprising at least one odor-diffusing device made up of at least one odor-diffusing support and a ventilator, the case further including a device for generating an air flow, an additional device for generating an additional air flow, and a heat treatment device, the at least one odor-diffusing device and the device for generating an air flow being arranged one above the other, wherein the heat treatment device is adapted and positioned to heat or cool air that passes through the additional device for generating an additional air flow.

15. A multisensory case comprising at least one odor-diffusing device made up of at least one odor-diffusing support and a ventilator, the case further including a device for generating an air flow, an additional device for generating an additional air flow, the at least one odor-diffusing device and the device for generating an air flow being arranged one above the other, and a plurality of sensory devices comprising a device for generating low-frequency sounds and a device for generating high-frequency sounds, wherein the plurality of sensory devices are arranged such that the device for generating low-frequency sounds is arranged below the device for generating an additional air flow, which in turn is arranged below the device for generating high-frequency sounds.

* * * * *